(12) United States Patent
Kato et al.

(10) Patent No.: US 10,961,888 B2
(45) Date of Patent: Mar. 30, 2021

(54) NOX SENSOR CONTROL DEVICE AND NOX SENSOR CONTROL METHOD

(71) Applicant: NGK SPARK PLUG CO., LTD., Nagoya (JP)

(72) Inventors: Kenji Kato, Nagoya (JP); Yuuya Nakayama, Nagoya (JP); Hirotaka Onogi, Nagoya (JP); Masao Tsuzuki, Nagoya (JP); Takumi Nishiyama, Nagoya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 156 days.

(21) Appl. No.: 16/406,111

(22) Filed: May 8, 2019

(65) Prior Publication Data

US 2019/0376425 A1    Dec. 12, 2019

(30) Foreign Application Priority Data

Jun. 8, 2018 (JP) .............................. JP2018-110023

(51) Int. Cl.
| | | |
|---|---|---|
| *F01N 3/00* | (2006.01) | |
| *F01N 3/08* | (2006.01) | |
| *F01N 11/00* | (2006.01) | |
| *F01N 3/20* | (2006.01) | |

(52) U.S. Cl.
CPC ........... *F01N 3/0885* (2013.01); *F01N 3/085* (2013.01); *F01N 3/2013* (2013.01); *F01N 11/007* (2013.01); *F01N 2570/04* (2013.01); *F01N 2900/1612* (2013.01)

(58) Field of Classification Search
CPC .. F01N 2560/026; F01N 3/0885; F01N 3/085; F01N 11/007; F01N 3/2013; F01N 2570/04; F01N 2900/1612
USPC .......................................................... 60/286
See application file for complete search history.

(56) References Cited

U.S. PATENT DOCUMENTS

| | | | |
|---|---|---|---|
| 2011/0016949 A1* | 1/2011 | Sasaki ................ | G01N 27/4175 73/23.31 |
| 2013/0034468 A1 | 2/2013 | Bisaiji | |
| 2016/0146085 A1* | 5/2016 | Mizutani ............... | F01N 11/007 60/274 |
| 2016/0208721 A1* | 7/2016 | Wakimoto ......... | G01N 33/0042 |
| 2016/0209353 A1* | 7/2016 | Aoki .................. | G01N 27/4067 |
| 2016/0223488 A1* | 8/2016 | Kayama ................. | G01N 27/41 |
| 2016/0265461 A1* | 9/2016 | Nishijima ............. | F01N 3/2066 |
| 2016/0290961 A1* | 10/2016 | Aoki .................. | G01N 27/4074 |
| 2017/0248539 A1* | 8/2017 | Matsuda ............ | G01N 27/4074 |

(Continued)

FOREIGN PATENT DOCUMENTS

WO     2013/018234 A1    2/2013

*Primary Examiner* — Jason D Shanske
(74) *Attorney, Agent, or Firm* — Sughrue Mion, PLLC

(57) ABSTRACT

A NOx sensor control device is connected to a NOx sensor mounted in an internal combustion engine. The NOx sensor has a detection cell configured to detect a NOx concentration and having a solid electrolyte body and a pair of electrodes provided on a surface of the solid electrolyte body and a heater heating the detection cell. The NOx sensor control device has a heater control unit. The heater control unit is configured to, at a time when an operation of the internal combustion engine stops, perform a recovery control of the NOx sensor which is an electric current control of the heater for removing SOx adsorbed to the NOx sensor.

11 Claims, 5 Drawing Sheets

(56) References Cited

U.S. PATENT DOCUMENTS

2017/0321588 A1\* 11/2017 Aoki ................... G01M 15/102
2019/0186325 A1\* 6/2019 Matsuda ................ G01N 27/41

\* cited by examiner

NOX SENSOR CONTROL DEVICE AND NOX SENSOR CONTROL METHOD

BACKGROUND OF THE INVENTION

The present invention relates to a NOx sensor control device connected to a NOx sensor that detects a concentration of NOx and also relates to a NOx sensor control method.

As a gas sensor used for an improvement in fuel efficiency of an internal combustion engine of a vehicle etc. and for a combustion control of the internal combustion engine, there are known an oxygen sensor and an air fuel ratio sensor that detect a concentration of oxygen in exhaust gas. Further, according to tightening of vehicle emission control, reduction in amount of nitrogen oxide (NOx) in the exhaust gas is required, and a NOx sensor that is capable of directly measuring a concentration of NOx has been developed.

As such NOx sensor, there is known a NOx sensor having a plurality of cells, each of which is formed by a solid electrolyte body, such as zirconia, having oxygen ion conductivity and a pair of electrodes provided on a surface of the solid electrolyte body. As the NOx sensor having the above configuration, a structure in which an oxygen pump cell and a detection cell are laminated is especially known. In this NOx sensor, an oxygen concentration in gas to be measured is controlled and maintained constant by the pump cell that faces a first measuring chamber into which the gas to be measured is introduced. The gas to be measured whose oxygen concentration is controlled flows into a second measuring chamber that communicates with the first measuring chamber. Then, by applying a constant voltage to the detection cell that faces the second measuring chamber, NOx in the gas to be measured is decomposed, and a current according to a NOx concentration flows in the detection cell, thereby detecting the NOx concentration on the basis of this current.

Here, the exhaust gas contains SOx (sulfur oxides), and it is known that the electrode of the cell forming the air fuel ratio sensor is poisoned by SOx, and this causes decrease in detection accuracy (Patent document 1: International Publication WO2013-018234). Patent document 1 discloses that the poisoning is detected by the fact that a variation of an air fuel ratio changes by the poisoning by SOx, and a poisoning recovery process that increases a temperature of the air fuel ratio sensor to an SOx decomposition temperature of about 650° C. is performed.

SUMMARY OF THE INVENTION

In the case of the NOx sensor, however, the NOx sensor detects the current passing through the electrodes of the detection cell when NOx (more specifically, NO) in the exhaust gas is decomposed into oxygen and $N_2$ under the constant voltage, and the electrodes of the detection cell for detecting the NOx concentration is highly susceptible to the poisoning by SOx as compared with the oxygen sensor such as the air fuel ratio sensor. It is thus difficult for the electrode to recover from the poisoning unless the sensor is heated for a long time. However, heating the sensor for a long time during an engine operation (an engine drive) brings a problem of not being able to detect the NOx concentration throughout the heating.

Therefore, an object of the present invention is to provide a NOx sensor control device and a NOx sensor control method, which are capable of surely removing SOx adsorbed to the NOx sensor without interfering with the detection of the NOx concentration during the operation of the internal combustion engine.

To solve the above problem, according to one aspect of the present invention, a NOx sensor control device connected to a NOx sensor mounted in an internal combustion engine, the NOx sensor having a detection cell configured to detect a NOx concentration and having a solid electrolyte body and a pair of electrodes provided on a surface of the solid electrolyte body and a heater heating the detection cell, the NOx sensor control device comprises: a heater control unit configured to, at a time when an operation of the internal combustion engine stops, perform a recovery control of the NOx sensor which is an electric current control of the heater for removing SOx adsorbed to the NOx sensor.

According to the NOx sensor control device, by performing the recovery control that heats the heater at the time when the operation of the internal combustion engine stops, it is possible to remove SOx adsorbed to the NOx sensor by the heating of the NOx sensor for a sufficient time without interfering with the detection of the NOx concentration during the operation of the internal combustion engine.

The heater control unit could be configured to, at the time when the operation of the internal combustion engine stops, control the heater so that a temperature of the heater becomes a second control temperature that is higher than a first control temperature of the heater during the operation of the internal combustion engine.

According to this NOx sensor control device, since the NOx sensor is heated at a higher temperature and recovered, SOx can surely be removed.

The heater control unit could be configured to judge, on the basis of an operation signal of the internal combustion engine, that the operation of the internal combustion engine stops.

According to this NOx sensor control device, it is possible to accurately detect the stop of the operation of the internal combustion engine from the operation signal and surely remove SOx when the operation of the internal combustion engine stops without interfering with the detection of the NOx concentration during the operation of the internal combustion engine.

The heater control unit could be configured to perform the recovery control at a predetermined timing with the operation of the internal combustion engine regarded as a stop.

According to this NOx sensor control device, it is possible to perform the recovery control regularly at a predetermined timing regardless of whether or not the actual stop of the operation of the internal combustion engine occurs.

The heater control unit could be configured to stop the recovery control when receiving an operation signal of the internal combustion engine.

According to this NOx sensor control device, since the recovery control is stopped when the internal combustion engine operates, the detection of the NOx concentration during the operation of the internal combustion engine is not interfered or interrupted.

The second control temperature could be set so that a temperature of the detection cell is 730° C. or higher.

According to this NOx sensor control device, since the NOx sensor is heated at a further higher temperature, SOx can surely be removed.

The NOx sensor further has an oxygen pump cell configured to perform pump-out and/or pump-in of oxygen between an inside and an outside of the NOx sensor, and the NOx sensor control device further comprises an oxygen pump cell control unit configured to operate the oxygen pump cell so as to pump out the oxygen from the NOx sensor when the heater control unit performs the recovery control.

By findings of inventors of the present invention, it is conceivable that SOx is in a state of $SO_4^{2-}$ when being adsorbed to the NOx sensor, whereas SOx is in a state of $SO_2$ (gas) when leaving from the NOx sensor. Therefore, the leaving of SOx from the NOx sensor is facilitated in a reduction atmosphere.

Thus, according to this NOx sensor control device, by pumping out the oxygen in gas to be measured, the gas to be measured is introduced into the NOx sensor with the oxygen concentration in the gas to be measured being lower. This can thus further facilitate SOx leaving in the reduction atmosphere.

The heater control unit could be configured to stop the control of the heater when a totalizing control time of the recovery control is a predetermined threshold value or more.

According to this NOx sensor control device, the totalizing control time, which is a time required to sufficiently complete an SOx removal process (the recovery process) by the recovery control, is counted, then the recovery control is completed when the totalizing control time is the predetermined threshold value or more. It is therefore possible to surely remove SOx.

Here, in the following description, a "recovery process counter" corresponds to the totalizing control time of the recovery control.

The heater control unit could be configured to set completion related information that indicates completion of the control when a totalizing control time of the recovery control is a predetermined threshold value or more, and the heater control unit could be configured to stop the recovery control on the basis of the completion related information when receiving no operation signal of the internal combustion engine after setting the completion related information.

If the completion related information is not provided, after completion of the recovery process, the recovery process is executed many times repeatedly and endlessly, for instance, during OFF of the operation of the internal combustion engine in the middle of the night, and this causes a waste of power. Therefore, according to this NOx sensor control device, by stopping the recovery control on the basis of the completion related information, it is possible to prevent the recovery process from being unnecessarily repeated during OFF of the operation of the internal combustion engine.

Here, in the following description, a "completion flag" corresponds to the completion related information. Further, the completion related information is not limited to information (the completion flag) indicating that the recovery process is completed, and as described later, could be information (a "control incompletion flag") indicating that the recovery process is not completed.

The heater control unit could be configured to set recovery process information that indicates that the recovery control is ongoing at present, and to continue totalizing a time until the timing comes. And, when the time is totalized until the timing comes, the heater control unit could be configured to clear the totalized time when starting the recovery process, and to continue performing the recovery control on the basis of the recovery process information.

In a case where the recovery control is executed at the predetermined timing, depending on whether or not the engine operates during execution of the recovery process, when the recovery process is interrupted, a completion time of the recovery process changes. Because of this, a start time of a subsequent recovery process after next timing is shifted.

Therefore, according to this NOx sensor control device, since the totalized time is cleared when starting the recovery control, next timing can be accurately counted without being affected by the shift of time due to interruption of the recovery process after starting the recovery control, and the subsequent recovery process can be executed every exact time. Further, if the time is cleared when starting the recovery control, the totalized time is returned to 0, and the control stands by again, then the recovery control is stopped. Therefore, by continuing performing the recovery control on the basis of the recovery process information, the recovery control can continue while solving the problem of not being able to proceed to the recovery process. It is therefore possible to execute the recovery process every exact time with stability while meeting the status.

Here, in the following description, a "recovery process-ongoing flag" corresponds to the recovery process information. Further, the recovery process information is not limited to information (the recovery process-ongoing flag) indicating that the recovery process is ongoing, and as described later, could be information (a "recovery process-not-ongoing flag") indicating that the recovery process is not ongoing.

According to another aspect of the present invention, a method of controlling a NOx sensor mounted in an internal combustion engine, the NOx sensor having a detection cell configured to detect a NOx concentration and having a solid electrolyte body and a pair of electrodes provided on a surface of the solid electrolyte body and a heater heating the detection cell, the method comprises: at a time when an operation of the internal combustion engine stops, performing an electric current control of the heater for removing SOx adsorbed to the NOx sensor.

According to the present invention, it is possible to remove SOx adsorbed to the NOx sensor without interfering with the detection of the NOx concentration during the operation of the internal combustion engine.

The other objects and features of this invention will become understood from the following description with reference to the accompanying drawings.

DETAILED DESCRIPTION OF THE INVENTION

An embodiment of the present invention will be explained below with reference to the drawings.

Figure 1:
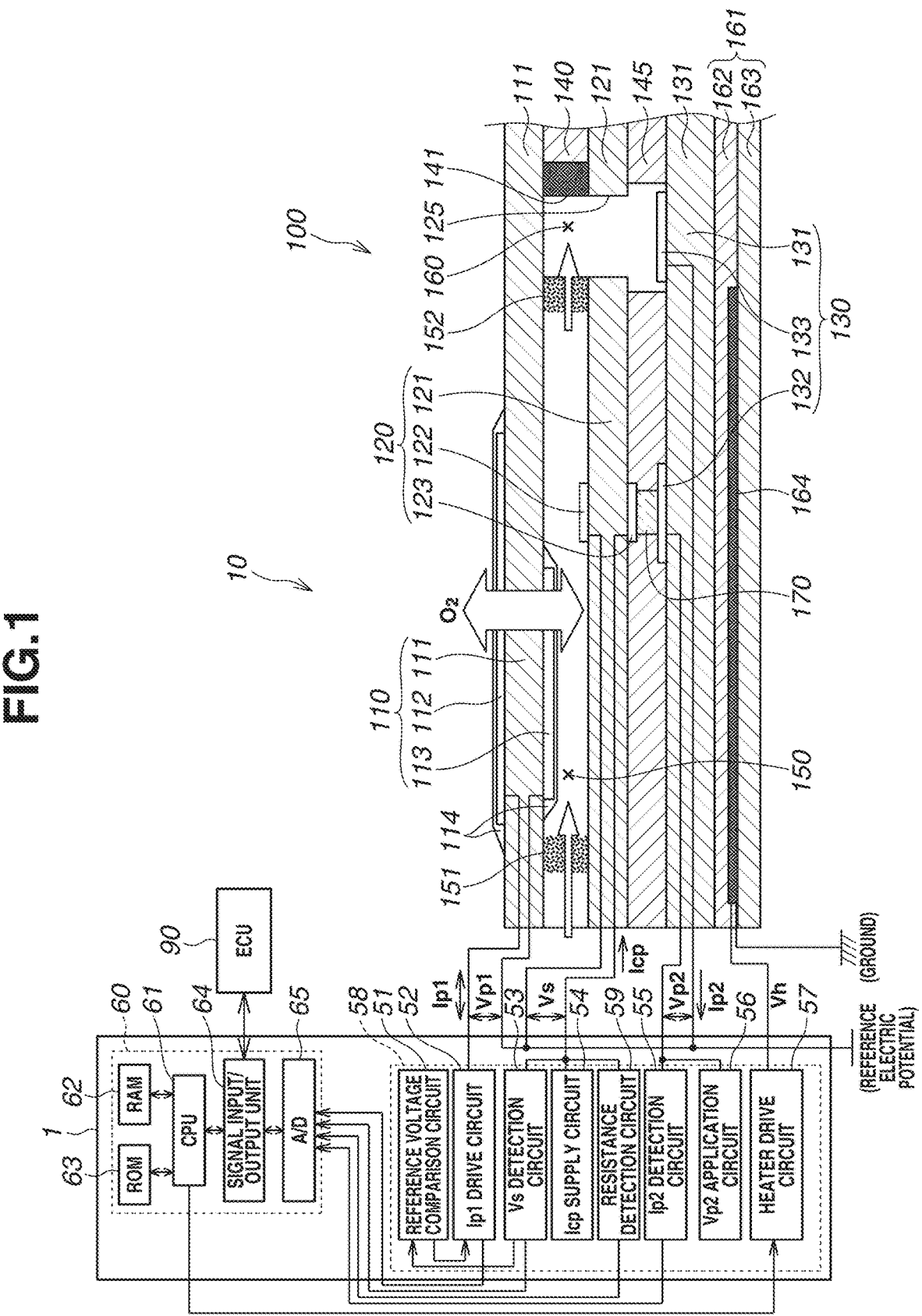
FIG. 1 is a block diagram showing configurations of a NOx sensor control device and a gas sensor connected to the NOx sensor control device, according to an embodiment of the present invention.

FIG. 1 is a block diagram showing configurations of a NOx sensor control device (a controller) 1 and a NOx sensor 10 connected to the NOx sensor control device 1. The NOx sensor control device 1 is mounted in a vehicle having an internal combustion engine (not shown, hereinafter, also called engine). The NOx sensor control device 1 is electrically connected to a connector (not shown) provided at the gas sensor (the NOx sensor) 10, and also electrically connected to a vehicle side control unit (ECU) 90 through a harness.

The NOx sensor control device 1 calculates a detection value (a concentration converted value) of a NOx concentration on the basis of a signal outputted from the NOx sensor 10, and outputs the detection value to the ECU 90. The ECU 90 performs a control of an engine operating condition, purification of NOx accumulated in a catalyst and detection of abnormality of the catalyst and so on, according to the NOx concentration.

First, a configuration of the NOx sensor 10 will be explained. The NOx sensor 10 has a sensor element 100. In FIG. 1, the sensor element 100 is shown as an internal cross-sectional view of a front end side part thereof. A side facing to the NOx sensor control device 1 is the front end side of the sensor element 100.

The sensor element 100 has a long narrow plate shape. The NOx sensor 10 is formed with this sensor element 100 held in a housing (not shown) that is fixed (mounted) in an engine exhaust pipe (not shown). Signal lines to transmit signals outputted from the sensor element 100 are drawn out from the NOx sensor 10, and electrically connected to the NOx sensor control device 1 that is fixed at a separate position from the NOx sensor 10.

The sensor element 100 has a layered structure or a stacked structure in which insulators 140 and 145 made of alumina etc. are sandwiched between three-layered plate-shaped solid electrolyte bodies 111, 121 and 131 respectively. Further, a heater element 161 is provided on an outer layer of the solid electrolyte body 131 side (which is opposite side to the solid electrolyte body 121 in FIG. 1). The heater element 161 is formed by laminated sheet-type insulation layers 162 and 163 having alumina as a main material and a heater pattern 164 having Pt as a main material and embedded between these insulation layers 162 and 163. Here, the heater element 161, which produces heat by the passage of electric current through the heater pattern 164, corresponds to a "heater" in claims.

The solid electrolyte bodies 111, 121 and 131 are made of zirconia that is a solid electrolyte, and have oxygen ion conductivity.

On both surfaces, in the stacking direction of the layers of the sensor element 100, of the solid electrolyte body 111, porous electrodes 112 and 113 are provided so as to sandwich the solid electrolyte body 111. These electrodes 112 and 113 are made of Pt or Pt alloy or cermet containing Pt and ceramics etc. Further, the electrodes 112 and 113 are provided, on surfaces thereof, with a ceramics-made porous protection layer 114. The protection layer 114 protects the electrodes 112 and 113 against deterioration caused by the fact that the electrodes 112 and 113 are exposed to poisoning gas (a reducing atmosphere) contained in the exhaust gas.

Then, by passing the electric current between or through the both electrodes 112 and 113, pump-out and pump-in of oxygen (so-called oxygen pumping) can be performed between an atmosphere (an external atmosphere to the sensor element 100) which the electrode 112 contacts and an atmosphere (an atmosphere in an after-mentioned first measuring chamber 150) which the electrode 113 contacts through the solid electrolyte body 111. In the present embodiment, the solid electrolyte body 111 and the electrodes 112 and 113 are called an Ip1 cell 110. Here, the Ip1 cell 110 corresponds to an "oxygen pump cell" in claims.

Next, the solid electrolyte body 121 is placed so as to face to the solid electrolyte body 111 with the insulator 140 sandwiched between the solid electrolyte body 111 and the solid electrolyte body 121. Also on both surfaces of this solid electrolyte body 121, porous electrodes 122 and 123 are provided so as to sandwich the solid electrolyte body 121. These electrodes 122 and 123 are made of Pt or Pt alloy or cermet containing Pt and ceramics etc., in the same manner as the electrodes 112 and 113. The electrode 122 is provided on the surface, facing to the solid electrolyte body 111, of the solid electrolyte body 121.

Between the solid electrolyte bodies 111 and 121, the hollow first measuring chamber 150 is formed as a small space. The electrode 113 at the solid electrolyte body 111 side and the electrode 122 at the solid electrolyte body 121 side are located in the first measuring chamber 150. This first measuring chamber 150 is the small space where the exhaust gas that flows in an exhaust passage (not shown) is first introduced into the sensor element 100.

At a front end side in the first measuring chamber 150 of the sensor element 100, porous first diffused resistor portion 151 that limits a flow amount of the exhaust gas flowing in the first measuring chamber 150 per unit of time is provided as a partition between an inside and an outside of the first measuring chamber 150. Likewise, at a rear end side in the first measuring chamber 150 of the sensor element 100, a second diffused resistor portion 152 that limits a flow amount of the exhaust gas per unit of time is provided as a partition between an opening 141 that communicates with an after-mentioned second measuring chamber 160 and the first measuring chamber 150.

The solid electrolyte body 121 and the electrodes 122 and 123 are a unit that can produce an electromotive force according to an oxygen partial pressure difference mainly between atmospheres (the atmosphere in the first measuring chamber 150 which the electrode 122 contacts and an atmosphere in an after-mentioned reference oxygen chamber 170 which the electrode 123 contacts) divided by the solid electrolyte body 121. In the present embodiment, the solid electrolyte body 121 and the electrodes 122 and 123 are called a Vs cell 120.

The Vs cell 120 also detects an internal resistance between the both electrodes 122 and 123.

Next, the solid electrolyte body 131 is placed so as to face to the solid electrolyte body 121 with the insulator 145 sandwiched between the solid electrolyte body 121 and the solid electrolyte body 131. Also on a surface, on the solid electrolyte body 121 side, of the solid electrolyte body 131, porous electrodes 132 and 133, made of cermet etc. containing Pt or Pt alloy or Pt and ceramics, are provided.

The insulator 145 is not provided at a position where the electrode 132 is formed, but the reference oxygen chamber 170 is formed as an isolated space. The electrode 123 of the Vs cell 120 is located in this reference oxygen chamber 170. The reference oxygen chamber 170 is filled with ceramic-made porous material. Further, the insulator 145 is not provided at a position where the electrode 133 is formed, but the hollow second measuring chamber 160 is formed as an isolated small space with the insulator 145 interposed between the reference oxygen chamber 170 and the second measuring chamber 160. The solid electrolyte body 121 and the insulator 140 are provided with openings 125 and 141 respectively so as to communicate with the second measuring chamber 160. Then, as mentioned above, the first measuring chamber 150 and the opening 141 are connected to each other with the second diffused resistor portion 152 arranged between these first measuring chamber 150 and opening 141.

The solid electrolyte body 131 and the electrodes 132 and 133 are a unit that can perform pump-out of oxygen between atmospheres (an atmosphere in the reference oxygen chamber 170 which the electrode 132 contacts and an atmosphere in the second measuring chamber 160 which the electrode 133 contacts) divided by the insulator 145, in the same manner as the Ip1 cell 110.

In the present embodiment, the solid electrolyte body 131 and the electrodes 132 and 133 are called an Ip2 cell 130. The Ip2 cell 130 that detects the NOx concentration corresponds to a "cell (more specifically, detection cell)" in claims. The electrodes 132 and 133 correspond to "a pair of electrodes" in claims.

Here, the electrode 113, located at the first measuring chamber 150 side, of the Ip1 cell 110, the electrode 122, located at the first measuring chamber 150 side, of the Vs cell 120 and the electrode 133, located at the second measuring chamber 160 side, of the Ip2 cell 130 are each connected to a reference electric potential in and by the controller 1. Further, one side electrode of the heater element 161 is grounded.

Next, a configuration of the NOx sensor control device 1 electrically connected to the sensor element 100 will be explained. The NOx sensor control device 1 has a microcomputer 60, an electric circuit unit 58 and so on. The microcomputer 60 has a CPU 61, a RAM 62, a ROM 63, an A/D converter 65, a signal input/output section (a signal input/output unit) 64 that communicates with the ECU 90 and is connected to the CPU 61 and the A/D converter 65, a timer clock (not shown) etc.

The electric circuit unit 58 is configured by a reference voltage comparison circuit 51, an Ip1 drive circuit 52, a Vs detection circuit 53, an Icp supply circuit 54, an Ip2 detection circuit 55, a Vp2 application circuit 56, a heater drive circuit 57 and a resistance detection circuit 59. The electric circuit unit 58 detects the NOx concentration in the exhaust gas using the NOx sensor 10 (the sensor element 100).

The Icp supply circuit 54 supplies or passes an electric current Icp between or through the electrodes 122 and 123 of the Vs cell 120, then performs the pump-out of oxygen from the first measuring chamber 150 into the reference oxygen chamber 170. The Vs detection circuit 53 is a circuit that detects a voltage Vs between the electrodes 122 and 123. The Vs detection circuit 53 outputs its detection result to the reference voltage comparison circuit 51. The reference voltage comparison circuit 51 is a circuit that compares the voltage Vs between the electrodes 122 and 123 of the Vs cell 120 detected by the Vs detection circuit 53 with a reference voltage (e.g. 425 mV) that is a reference. The reference voltage comparison circuit 51 outputs its comparison result to the Ip1 drive circuit 52.

The Ip1 drive circuit 52 is a circuit that supplies or passes an electric current Ip1 between or through the electrodes 112 and 113 of the Ip1 cell 110. A magnitude and a direction of the electric current Ip1 are adjusted on the basis of the comparison result between the voltage Vs and the reference voltage by the reference voltage comparison circuit 51 so that a voltage between the electrodes 122 and 123 of the Vs cell 120 is substantially equal to a predetermined reference voltage. By the current supply by the Ip1 drive circuit 52 with adjustment of the magnitude and direction of the electric current, the pump-out of oxygen from the first measuring chamber 150 to the outside of the sensor element 100 and the pump-in of oxygen from the outside of the sensor element 100 into the first measuring chamber 150 are performed by the Ip1 cell 110. That is, the Ip1 cell 110 adjusts an oxygen concentration in the first measuring chamber 150 so that the voltage between the electrodes 122 and 123 of the Vs cell 120 is kept at a constant value (a value of the reference voltage).

Here, the Ip1 drive circuit 52 and the CPU 61 correspond to an "oxygen pump cell control unit" of the present invention.

The Vp2 application circuit 56 is a circuit that applies a constant voltage Vp2 (e.g. 450 mV), which decomposes NOx (more specifically, NO) in gas to be measured (namely, in the exhaust gas) into oxygen and $N_2$, between the electrodes 132 and 133 of the Ip2 cell 130. The Vp2 application circuit 56 decomposes NOx into nitrogen and oxygen, and performs the pump-out oxygen from the second measuring chamber 160 into the reference oxygen chamber 170 (from the electrode 133 to the electrode 132). The Ip2 detection circuit 55 is a circuit that detects a value of an electric current Ip2 flowing between the electrodes 132 and 133 of the Ip2 cell 130.

The heater drive circuit 57 is controlled by the CPU 61. The heater drive circuit 57 is a circuit that passes an electric current through the heater pattern 164 of the heater element 161 and heats the solid electrolyte bodies 111, 121 and 131 (i.e. the Ip1 cell 110, the Vs cell 120 and the Ip2 cell 130), and also holds temperatures of the solid electrolyte bodies 111, 121 and 131 at a predetermined temperature (in other words, a target temperature or a target value). The heater pattern 164 is a single electrode pattern extending in the heater element 161, and one end portion of the heater pattern 164 is grounded, and the other end is connected to the heater drive circuit 57.

This heater drive circuit 57 and the CPU 61 are configured to control the electric current flowing in the heater pattern 164 by a PWM current application control of the heater pattern 164 on the basis of an after-mentioned internal resistance value of the Vs cell 120 so that the temperatures of the solid electrolyte bodies 111, 121 and 131 (more specifically, the temperature of the solid electrolyte body 121 in the present embodiment) become the target temperature.

Here, the heater drive circuit 57 and the CPU 61 correspond to a "heater control unit" of the present invention.

Next, a measuring method of the internal resistance (an impedance) of the Vs cell 120 according to the present embodiment will be explained. This measurement of the internal resistance of the Vs cell 120 is carried out at predetermined regular time intervals. As the measuring method of the internal resistance (the internal resistance value) of the Vs cell 120, by passing a constant current I between or through the electrodes 122 and 123 formed at the Vs cell 120 from a constant-current source circuit that forms the resistance detection circuit 59 for a certain time, a voltage V between the electrodes 122 and 123 changes in response to the flow of the constant current I, and the resistance detection circuit 59 measures this voltage V. Then, on the basis of a variation of the voltage V when the constant current I flows and the constant current I, the CPU 61 of the microcomputer 60 calculates the value of the internal resistance.

More specifically, the CPU 61 inputs, through the resistance detection circuit 59, a voltage between the electrodes 122 and 123 before passing the constant current I through the Vs cell 120 from the constant-current source circuit provided in the resistance detection circuit 59 and a voltage between the electrodes 122 and 123 after a lapse of a certain time (e.g. after a lapse of 60 μs) after passing the constant current I through the Vs cell 120 from the constant-current source circuit, and determines the value of the internal resistance of the Vs cell 120 from a voltage difference (the variation) LV between the inputted two voltages using a previously-set formula or a predetermined map.

Since a circuit configuration of this resistance detection circuit 59 and the measuring method of the internal resistance of the Vs cell 120 are well known, these detailed explanations will not be made any longer.

Here, in the same manner as the measurement of the internal resistance of the Vs cell 120, internal resistances of the Ip1 cell 110 and the Ip2 cell 130 can also be measured.

Next, a detecting operation of the NOx concentration by the NOx sensor control device 1 having the above configuration will be explained.

First, the solid electrolyte bodies 111, 121 and 131 forming the sensor element 100 are heated by and according to temperature increase of the heater pattern 164 in which a drive current from the heater drive circuit 57 flows, and are activated. With this, each of the Ip1 cell 110, the Vs cell 120 and the Ip2 cell 130 functions.

On the other hand, the exhaust gas flowing in the exhaust passage (not shown) is introduced in the first measuring chamber 150 while undergoing the limitation of the flow amount by the first diffused resistor portion 151. Here, a weak electric current Icp flows in the Vs cell 120 from the electrode 123 side to the electrode 122 side by the Icp supply circuit 54. Because of this, oxygen in the exhaust gas can receive electrons from the electrode 122, which is a negative electrode side, in the first measuring chamber 150, and becomes an oxygen ion. And, the oxygen ion flows in the solid electrolyte body 121, and moves to an inside of the reference oxygen chamber 170. That is, by the fact that the electric current Icp flows between the electrodes 122 and 123, oxygen in the first measuring chamber 150 enters the reference oxygen chamber 170, and the electrode 123 functions as a reference electrode.

The Vs detection circuit 53 has detected the voltage Vs between the electrodes 122 and 123, and this voltage is compared with the reference voltage (425 mV) by the reference voltage comparison circuit 51, then this comparison result is outputted to the Ip1 drive circuit 52. Here, by adjusting the oxygen concentration in the first measuring chamber 150 so that a potential difference (i.e. the voltage) between the electrodes 122 and 123 becomes constant around 425 mV, the oxygen concentration in the exhaust gas in the first measuring chamber 150 is brought close to a predetermined value (e.g. $10^{-8}$ to $10^{-9}$ atm).

Therefore, when the oxygen concentration in the exhaust gas introduced into the first measuring chamber 150 is lower than the predetermined value, the Ip1 drive circuit 52 passes the electric current Ip1 through the Ip1 cell 110 with the electrode 112 side being a negative electrode, and the pump-in of oxygen from the outside of the sensor element 100 into the first measuring chamber 150 is performed. On the other hand, when the oxygen concentration in the exhaust gas introduced into the first measuring chamber 150 is higher than the predetermined value, the Ip1 drive circuit 52 passes the electric current Ip1 through the Ip1 cell 110 with the electrode 113 side being a negative electrode, and the pump-out of oxygen from the first measuring chamber 150 to the outside of the sensor element 100 is performed.

As described above, the exhaust gas whose oxygen concentration is adjusted in the first measuring chamber 150 is introduced into the second measuring chamber 160 through the second diffused resistor portion 152. NOx, which contacts the electrode 133 in the second measuring chamber 160, in the exhaust gas is decomposed (reduced) into $N_2$ and $O_2$ with the electrode 133 being a catalyst. The decomposed oxygen receives electrons from the electrode 133, and becomes an oxygen ion. And, the oxygen ion flows in the solid electrolyte body 131, and further moves to the electrode 132. At this time, residual oxygen which remains in the first measuring chamber 150 by the pimping also moves into the reference oxygen chamber 170 by the Ip2 cell 130. Therefore, an electric current flowing in the Ip2 cell 130 is an electric current that comes from NOx and comes from the residual oxygen.

Here, since a concentration of the residual oxygen remaining in the first measuring chamber 150 by the pumping has been adjusted to the predetermined value as described above, the electric current coming from this residual oxygen can be considered to be substantially constant. Therefore, the electric current coming from the residual oxygen has little influence on a variation of the electric current coming from NOx, and thus the electric current flowing in the Ip2 cell 130 is proportional to the NOx concentration. In the NOx sensor control device 1, the Ip2 detection circuit 55 detects the electric current Ip2 flowing in the Ip2 cell 130, and the microcomputer 60 performs, from the detected electric current value, a well-known correction calculation operation of an offset current that comes from the residual oxygen, and detects the NOx concentration in the exhaust gas.

Next, a control operation of the heater to remove SOx adsorbed to the NOx sensor 10 (more specifically, the electrode 133 of the Ip2 cell 130) will be explained.

If SOx (sulfur oxides) is contained in the gas to be measured such as the exhaust gas, SOx is adsorbed to the electrode 133 of the Ip2 cell 130, and a response of the Ip2 cell 130 is deteriorated. And, it has been found that when the electrode 133 is heated at a predetermined temperature or higher for a predetermined time or more (for instance, at 700° C. or higher for three minutes or more), SOx adsorbed to the electrode 133 leaves from the electrode 133 and is removed, then the response of the Ip2 cell 130 recovers.

Further, it has been found that when SOx reacts with oxygen, SOx easily leaves from the electrode 133.

Therefore, in the present invention, by heating the heater element 161 at a time when the operation of the internal combustion engine stops (the engine drive stops), it is possible to remove SOx adsorbed to the NOx sensor (the electrode 133) by the heating of the NOx sensor (the sensor element 100) for a sufficient time without interfering with the detection of the NOx concentration during the operation of the internal combustion engine.

Here, the stop of the operation of the internal combustion engine (the engine drive stop) means stop of the internal combustion engine by OFF of an engine key or a switch by driver's intention, except for an automatic idle-stop.

A specific heat application control (a current application control) of the heater element 161 in a recovery control can be performed by monitoring the above-mentioned internal resistance value of the Vs cell 120. More specifically, since the internal resistance value of the Vs cell 120 decreases with increase in the temperature of the NOx sensor 10 (the sensor element 100), a setting internal resistance value (this corresponds to a control temperature of the heater element 161) of the Vs cell 120 when heating the heater element 161 by the current application is previously determined, then the current application of the heater element 161 is controlled so that the internal resistance value of the Vs cell 120 becomes this setting internal resistance value.

When the application of heat of the heater element 161 is controlled at the time of the engine stop so that the temperature of the heater element 161 becomes a second control temperature (e.g. 700° C.) that is higher than a first control temperature (e.g. 655° C.) of the heater during the operation of the internal combustion engine, since the NOx sensor 10 is heated at a higher temperature, SOx can surely be removed. Here, as described above, each control temperature corresponds to the setting internal resistance value of the Vs cell 120.

It is preferable to set the second control temperature so that a temperature of the Ip2 cell 130 is 730° C. or higher, because SOx leaves from the electrode 133 more. However, if the second control temperature is too high, there is a risk that the NOx sensor 10 itself will be deteriorated. Therefore, it is preferable to set the second control temperature so that a maximum temperature of the NOx sensor 10 is 1000° C. or lower.

Further, when oxygen is pumped out from the first measuring chamber 150 by the operation of the oxygen pump cell (the Ip1 cell 110) during operation of the recovery control (the control of the heater element 161), since the gas to be measured is introduced into the electrode 133 with the oxygen concentration in the gas to be measured being lower, this can further facilitate SOx leaving in a reduction atmosphere.

Here, a control of the pump-out of oxygen from the first measuring chamber 150 is carried out in the same manner as the detecting operation of the NOx concentration. That is, the voltage detected by the Vs detection circuit 53 is compared with the reference voltage (425 mV) by the reference voltage comparison circuit 51. And, the oxygen concentration in the first measuring chamber 150 is adjusted so that the potential difference (i.e. the voltage) between the electrodes 122 and 123 i.e. becomes constant around 425 mV.

At this time, during stop of the operation of the internal combustion engine, ambient air of the NOx sensor 10 (i.e. air in an exhaust pipe) and air in the first measuring chamber 150 are the atmospheric air whose oxygen concentration is higher than that in the exhaust gas. Therefore, the above control is carried out so that the pump-in of oxygen into the first measuring chamber 150 is not performed, but the pump-out of oxygen from the first measuring chamber 150 is performed.

Figure 2:
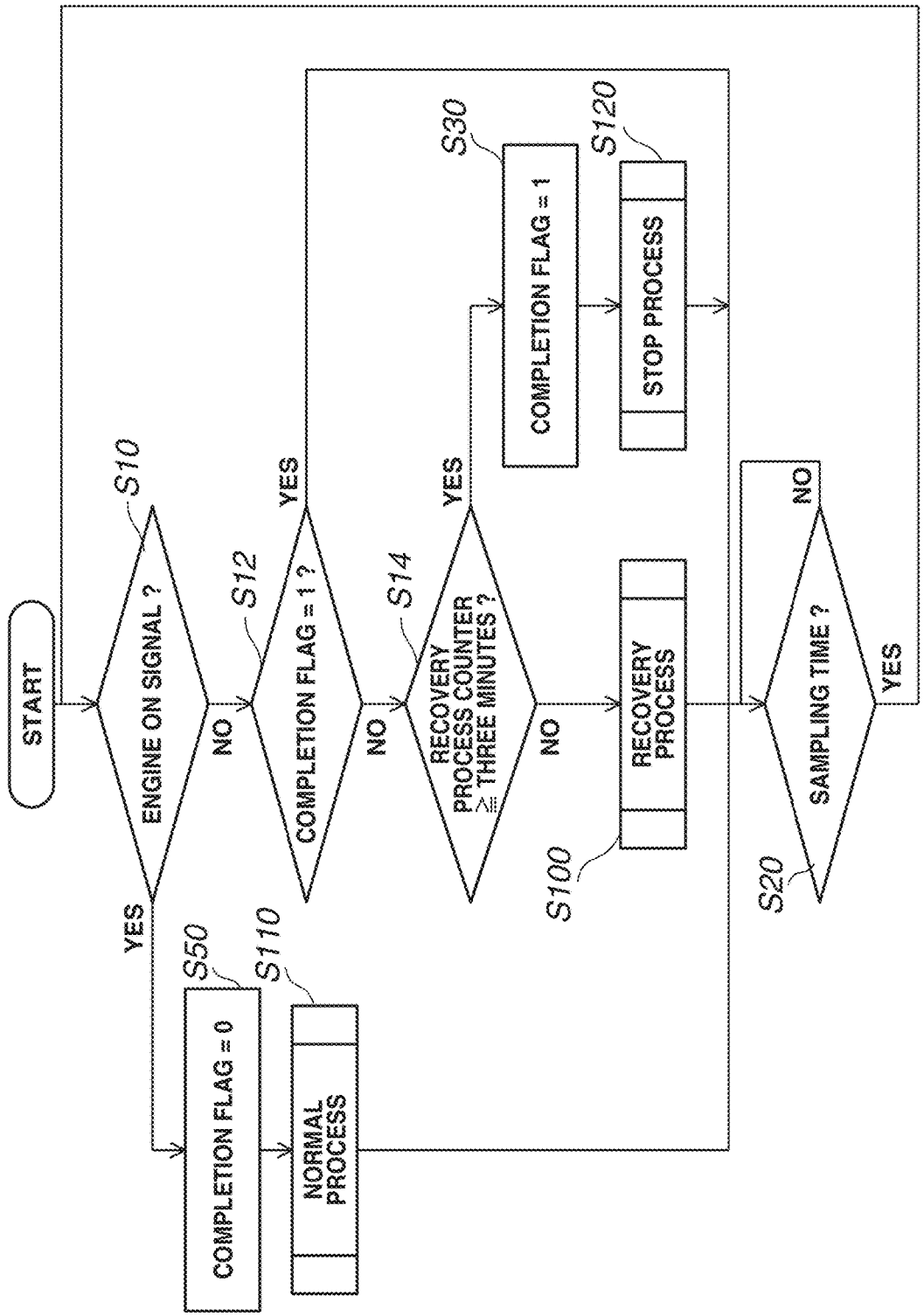
FIG. 2 is a drawing showing a flow of a recovery control process when judging that an engine operation stops on the basis of an engine operation signal.
Figure 3:
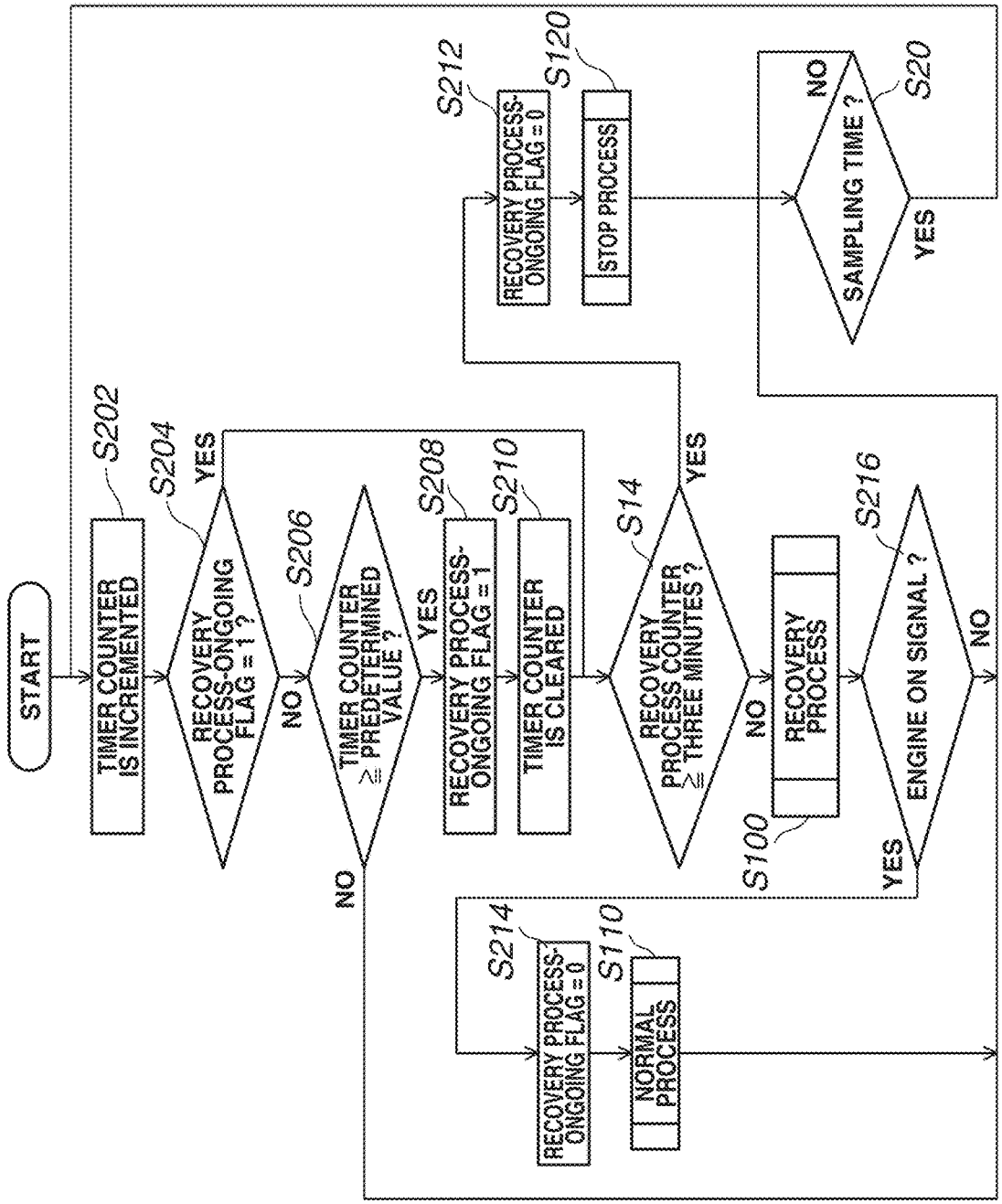
FIG. 3 is a drawing showing a flow of a recovery control process when judging, at a predetermined timing, that the engine operation stops.

Next, specific control operations of the heater and the oxygen pump cell in the recovery control will be explained with reference to FIGS. 2 and 3. FIG. 2 shows a drawing of a flow of a recovery control process when judging that the engine operation stops on the basis of an engine operation signal. FIG. 3 shows a drawing of a flow of a recovery control process when judging, at a predetermined timing, that the engine operation stops.

In the flow shown in FIG. 2, first, the CPU 61 judges whether or not the engine is ON (an operating state) on the basis of the engine operation signal (step S10). More specifically, at step S10, for instance, by detecting the presence or absence of an ACC (accessory) current that flows when operating the engine by ON of an ignition key or a switch, the engine operation can be judged. That is, when the ACC current flows, the engine ON is judged, whereas when the ACC current does not flow, the engine OFF is judged. The ACC current corresponds to an "operation signal of the internal combustion engine" in claims.

If NO at step S10, the CPU 61 judges whether or not a completion flag is 1 ("completion flag=1") (step S12).

If NO at step S12, the CPU 61 judges whether or not a recovery process counter is three minutes or more ("recovery process counter≥three minutes) (step S14).

This recovery process counter is a counter of time required to sufficiently complete an SOx removal process (the recovery process) by the heater control operation (the flow of FIG. 2). For instance, when the current application of the heater is done continuously for three minutes or more at step S18 (FIG. 4), the CPU 61 regards this as completion of the recovery process. The "three minutes" is set as a judgement reference of the counter at step S14.

The completion flag at step S12 indicates a status of completion of the recovery process by the above three minutes or more continuous recovery process. Meaning of setting of the completion flag is the following. That is, if the judgment at step S12 is not made, although the routine returns to step S10 after the recovery process at step S18 and S19 is completed, if the engine is OFF at this time, the recovery process is executed many times repeatedly and endlessly (with multiples of three minutes) (for instance, during engine OFF in the middle of the night).

Therefore, if YES at step S12, it is judged that the recovery process has been completed, then judged that there is no need to execute the recovery again. The routine then proceeds to step S20, and stands by. With this, the repeat of the recovery process during engine OFF is prevented.

Thus, if NO at step S14, since a totalizing time of the recovery process is less than three minutes and the recovery process is not completed, the routine proceeds to a subroutine of the recovery process at step S100.

Figure 4:
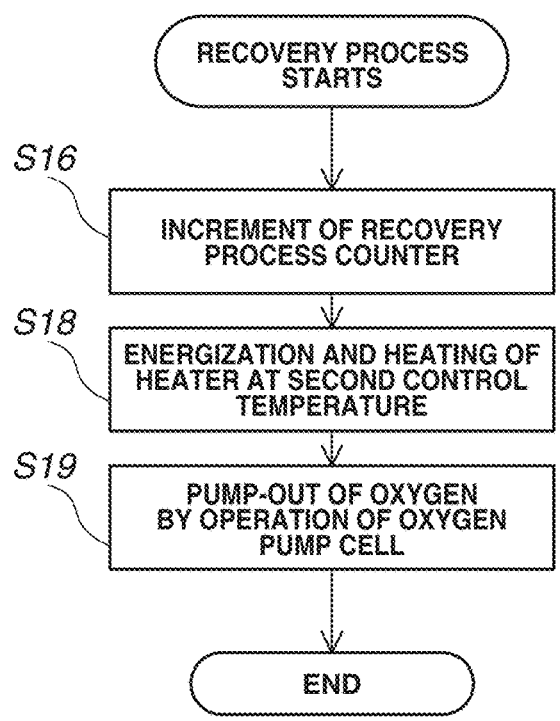
FIG. 4 is a drawing showing a sub-routine of a recovery process of FIGS. 2 and 3.

As shown in FIG. 4, in the sub-routine of step S100, at step S16, the recovery process counter is incremented by the CPU 61, and time of the recovery process is totalized or counted.

At step S18 subsequent to step S16, the CPU 61 performs the control that passes the electric current through the heater element 161 and heats the heater element 161 at the second control temperature.

At step S19 subsequent to step S18, the CPU 61 performs the pump-out of oxygen from the first measuring chamber 150 by the operation of the oxygen pump cell (the Ip1 cell 110). Then, the sub-routine of step S100 is ended.

Next, at step S20 (FIG. 2) subsequent to the sub-routine of step S100, the CPU 61 judges whether or not next sampling time comes. If NO at step S20, the CPU 61 stands by until the next sampling time comes. Then, when the next sampling time comes (if YES at step S20), the routine returns to step S10.

Steps S16 to S20 are repeated in this manner, then the recovery process continuously proceeds, and the time of the recovery process is totalized or counted.

On the other hand, if YES at step S10, i.e. if the engine is ON, even if the completion flag is 1. ("completion flag=1") at this time, the routine proceeds to step S50 and the CPU 61 sets the completion flag to 0 ("completion flag=0") in order to execute the recovery process at a time when the engine is OFF next time.

Subsequently to step S50, the routine proceeds to a sub-routine of a normal process at step S110. The sub-routine of step S110 is a process that heats the heater at a normal heater control temperature.

Figure 5:
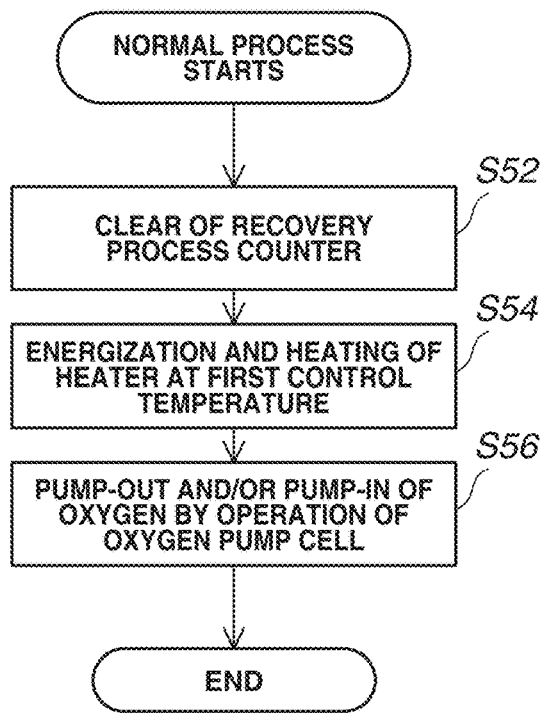
FIG. 5 is a drawing showing a sub-routine of a normal process of FIGS. 2 and 3.

As shown in FIG. 5, in the sub-routine of step S110, at step S52, the CPU 61 clears or resets the recovery process counter. By clearing the recovery process counter, the totalizing time of the recovery process is returned to zero, and the recovery process can be resumed when the engine is OFF next time.

At step S54 subsequent to step S52, the CPU 61 performs the control that passes the electric current through the heater element 161 and heats the heater element 161 at the first control temperature (i.e. the normal heater control temperature).

At step S56 subsequent to step S54, the CPU 61 performs the pump-out of oxygen from the first measuring chamber 150 and/or the pump-in of oxygen into the first measuring chamber 150 by the operation of the oxygen pump cell (the Ip1 cell 110) so that the voltage Vs is substantially equal to the reference voltage. Here, regarding the step S56, since the operation of the oxygen pump cell stops in a following sub-routine of stop process at step S120 in FIG. 2, by the step S56, the oxygen pump cell is operated at a time when the engine is ON after the stop of the operation of the oxygen pump cell by the stop process.

Afterwards, the sub-routine of step S110 is ended, and the routine proceeds to step S20.

On the other hand, if YES at step S14, since the recovery process is completed, the CPU 61 sets the completion flag to 1 ("completion flag=1") (step S30), and the routine proceeds to the sub-routine of stop process at step S120. The sub-routine of the stop process is processes that stops the current application of the heater and the control of the oxygen pump cell (the Ip1 cell 110).

Figure 6:
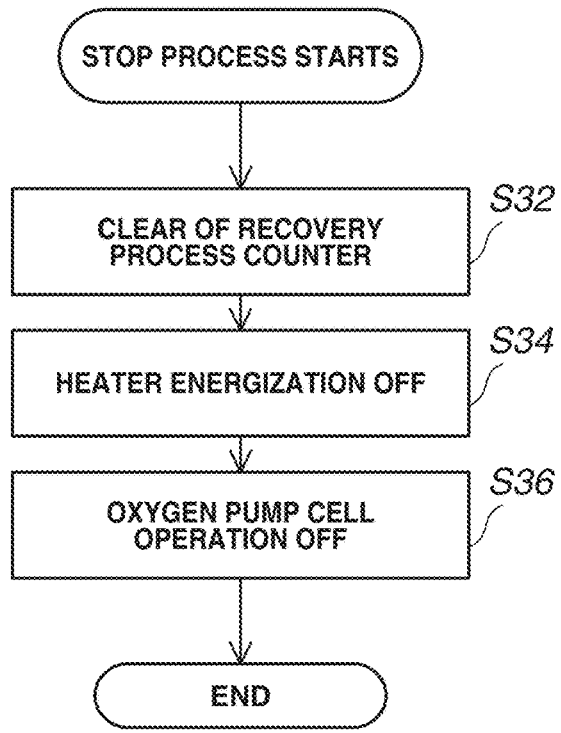
FIG. 6 is a drawing showing a sub-routine of a stop process of FIGS. 2 and 3.

As shown in FIG. 6, in the sub-routine of step S120, at step S32, the CPU 61 clears or resets the recovery process counter. Subsequently, at step S34, the CPU 61 performs the control that stops the current application of the heater element 161 ("heater current application OFF"). Further, at step S36, the CPU 61 performs the control that stops the operation of the oxygen pump cell (the Ip1 cell 110). Afterwards, the routine proceeds to step S20.

The flow shown in FIG. 3 is a flow that performs the control of the heater element 161 regularly at a predetermined timing (a predetermined time) regardless of whether or not the actual engine OFF occurs. The predetermined time (the predetermined timing) could be a predetermined time (every two hours with 0 a.m. (midnight) being a reference) using the timer clock of the microcomputer 60. Or, a start time or an end time of the last control of the heater element 161 is previously stored, then the predetermined timing could be determined as a timing when a time (e.g. two hours) elapses from the start time or the end time.

In the flow shown in FIG. 3, first, in order to judge whether or not the predetermined timing (the predetermined time) comes, a timer counter is incremented by the CPU 61 (step S202).

The timer counter is incremented at step S202, and time is totalized or counted until the predetermined timing comes.

In the flow shown in FIG. 3, the same step as that in FIG. 2 is denoted by the same reference sign, and its explanation will be omitted here.

Subsequently to step S202, the CPU 61 judges whether or not a recovery process-ongoing flag is 1 ("recovery process-ongoing flag=1") (step S204).

This "recovery process-ongoing flag=1" indicates that the recovery process is ongoing or in progress now. The recovery process-ongoing flag is used to judge when to clear the timer counter of step S202. That is, for instance, in a case where the timer counter is totalized or counted and the recovery process is executed every certain time (six hours), the timer counter is cleared at any timing during execution of the recovery process, then next certain time is measured or counted.

Figure 7:
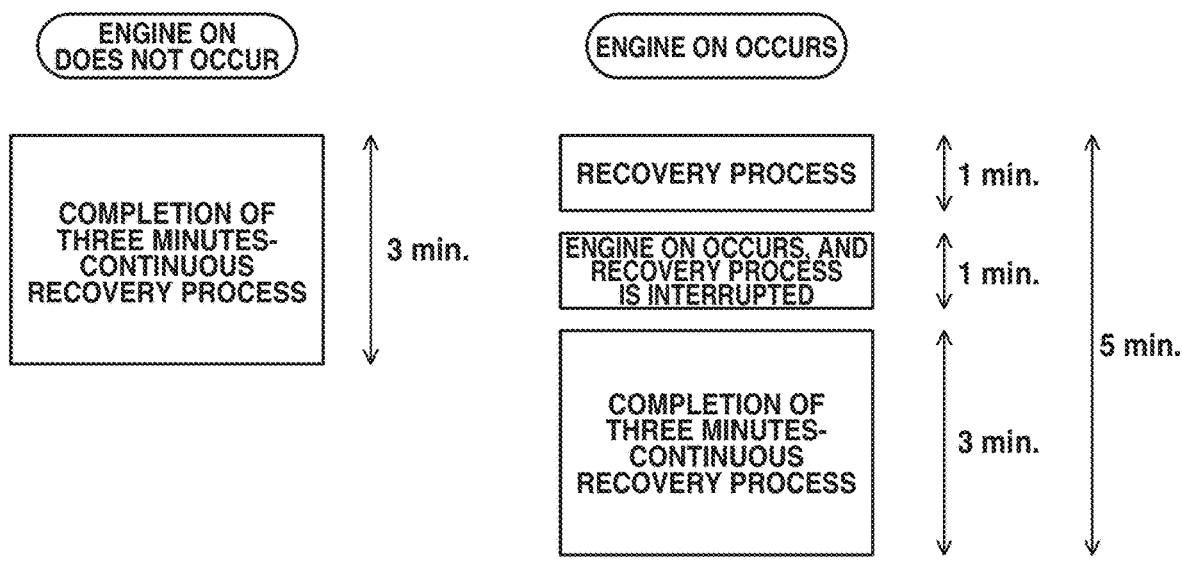
FIG. 7 is a drawing showing a difference (or a shift) of a start time of the recovery process in the recovery control of FIG. 3.

Here, it is noted that in the case where the recovery process is executed every predetermined timing (every predetermined time) like the flow shown in FIG. 3, depending on a status of the engine which indicates whether or not the engine ON occurs (step S216) during execution of the recovery process (i.e. while the recovery process is in progress), as shown in FIG. 7, a start time of a subsequent recovery process (step S100) is shifted.

More specifically, in FIG. 7, if the engine ON does not occur during execution of the recovery process, a time required from start to completion of the recovery process is three minutes. On the other hand, in a case where the engine ON occurs when one minute elapses from start of the recovery process and this engine ON continues for one minute, because the recovery process does not continue for three minutes or more, the recovery process is executed again for three minutes after the engine is OFF from the engine ON. Consequently, the recovery process is completed at this time, then it takes total five minutes from start to completion of the recovery process. Because of this, a start time of the subsequent recovery process after a lapse of a standby time of the next certain time (six hours) is shifted by 2 minutes.

Although the recovery process is possible even if this shift of time occurs, it is preferable that this shift of time be eliminated and the recovery process be executed exactly every certain time (six hours).

To eliminate this shift, the point is a position where a step of "clear the timer counter" (step S216) is placed. For instance, in a case where the timer counter is cleared at either step before or after step S120 after completion of the recovery process (e.g. after three minutes elapses) like YES of step S14 in FIG. 3, the timer counter is cleared after "three minutes" elapses when the engine ON does not occur in FIG. 7 or after "five minutes" elapses when the engine ON occurs in FIG. 7. Hence, in the end, it is not possible to eliminate the shift of time due to the difference of the status by the presence or absence of the engine ON.

Thus, if the timer counter is cleared at a timing when the recovery process is started, like step S210 in FIG. 3, the timer counter is cleared at time 0 of the start of the recovery process in FIG. 7. Therefore, the start time of the subsequent recovery process is not shifted without being affected by an interruption of the recovery process due to the engine ON occurring afterwards.

However, in this case, this time, a problem that the recovery process does not proceed arises. That is, in the flow in FIG. 3, if the "recovery process-ongoing flag" is ignored, at first, the timer counter is incremented and time is counted at step S202, and after a lapse of the certain time (six hours), the timer counter is cleared at step S210, then the routine proceeds to the recovery process at steps S14 and S100.

Then, although when the next sampling time comes at step S20, the routine returns to step S202 and the increment of the timer counter is started, since the timer counter is not sufficiently totalized or counted at this time, NO is selected at step S206, then the routine cannot proceed to step S14 where the recovery process is executed. Therefore, the problem that this routine is repeated and cannot proceed to the recovery process until the timer counter is sufficiently totalized or counted, i.e. the recovery process is executed only at one sampling time, arises.

Therefore, by introducing the "recovery process-ongoing flag" as step S208, if the recovery process-ongoing flag is 1

("recovery process-ongoing flag=1") at step S204 to which the routine returns after the recovery process is executed at a first sampling time, the routine can directly proceed to step S14 where the recovery process is executed without through step S206. That is, the timer counter can be cleared at the timing when the recovery process is started, and the recovery process can continue while solving the problem of not being able to proceed to the recovery process. It is therefore possible to execute the recovery process every exact time with stability while meeting the status.

More specifically, If YES at step S204, i.e. if the recovery process is ongoing now, in order for the recovery to continue, the routine proceeds to step S14. And, if NO at step S14, the recovery process of the sub-routine at S100 is executed. Subsequently to the sub-routine at S100, the CPU 61 judges whether or not the engine is ON (the operating state) (step S216).

Here, if YES at step S216, i.e. if the engine ON is judged, since there is a need to stop the recovery process and clear the timer counter, the CPU 61 sets the recovery process-ongoing flag to 0 ("recovery process-ongoing flag=0") (step S214), and the routine proceeds to the normal process at step S110. After the normal process is ended, the routine proceeds to step S20.

On the other hand, If NO at step S216, since the predetermined timing (six hours) does not elapse, the routine proceeds to step S20, and a judgment of the next sampling time is made.

If NO at step S20, the CPU 61 stands by until the next sampling time comes. Then, when the next sampling time comes (if YES at step S20), the routine returns to step S202.

On the other hand, If NO at step S204, since the recovery process is not ongoing now, the CPU 61 judges whether or not the timer counter is a predetermined value (e.g. the above certain time (six hours)) or more (step S206).

If NO at step S206, since the predetermined timing (six hours) does not elapse, the routine proceeds to step S20, and a judgment of the next sampling time is made.

On the other hand, If YES at step S206, since the predetermined timing (six hours) elapses, in order to execute the recovery process every certain time (six hours), the CPU 61 sets the recovery process-ongoing flag to 1 ("recovery process-ongoing flag=1") (step S208), and clears the timer counter (step S210). And, to execute the recovery, the routine proceed to step S14.

Here, If YES at step S14, since the recovery process is completed, the CPU 61 sets the recovery process-ongoing flag to 0 ("recovery process-ongoing flag=0") (step S212), and the routine proceeds to the sub-routine of stop process at step S120. Subsequently to the sub-routine of stop process at step S120, the routine proceeds to step S20.

As described above, (i) as long as NO is selected at step S206, i.e. until the predetermined timing (six hours) elapses, a leftmost flow in FIG. 3 is repeated, and the timer counter is counted.

(ii) Then, If YES at step 206, i.e. if the predetermined timing (six hours) elapses, the recovery process-ongoing flag is set to 1 ("recovery process-ongoing flag=1") at step S208, and the timer counter is cleared, then the recovery process is started (step S100). When the recovery process is in progress, the recovery process-ongoing flag is maintained at 1 ("recovery process-ongoing flag=1" is maintained), and a middle flow in FIG. 3 is repeated, and also the recovery process counter and the timer counter are totalized or counted.

(iii) If the engine is ON during execution of the recovery process (i.e. while the recovery process is in progress), the recovery process-ongoing flag is set to 0, and the recovery process counter is cleared, then the recovery process is stopped. The routine then proceeds to the normal process (step S110).

(iv) Further, if the recovery process counter is three minutes or more (step S14), i.e. if the recovery process is completed, the recovery process-ongoing flag is set to 0, and in order to end the recovery process, the routine proceeds to the stop process (step S120). Then, until the predetermined timing (six hours) elapses from the start time of the last recovery process, processes to return to (i) are repeated.

The present invention is not limited to the above embodiment, and includes all design modifications and equivalents belonging to the technical scope of the present invention.

For instance, the heater control unit and the oxygen pump cell control unit could be provided in an external device (ECU), then the ECU could perform the control of the heater and the oxygen pump cell.

Further, in the above embodiment, the oxygen pump cell during execution of the recovery process is controlled so that the voltage Vs is substantially equal to the reference voltage, in the same manner as the normal control.

However, for instance, a setting table in which a magnitude or a direction of the electric current $Ip1$ for the pump-out of oxygen from the first measuring chamber are set could be previously provided, then the oxygen could be pumped out from the first measuring chamber during execution of the recovery process using this setting table.

Furthermore, in the above embodiment, when the recovery process is completed, the heater control unit sets the completion flag to 1, which indicates the completion of the recovery process, and the recovery process is stopped according to this completion flag. However, a control incompletion flag, which indicates that the recovery process is not completed, might be set, and when the recovery process is completed, this control incompletion flag is reset, then the recovery process could be stopped according to the control incompletion flag (the control incompletion flag=0).

With regard to the recovery process-ongoing flag, likewise, for instance, a recovery process-not-ongoing flag, which indicates that the recovery process is not ongoing, might be set, and the recovery process flow could proceed according to the recovery process-not-ongoing flag (the recovery process-not-ongoing flag=0).

EXPLANATION OF REFERENCE

1 . . . NOx sensor control device
10 . . . NOx sensor
52, 61 . . . Ip1 drive circuit, CPU (oxygen pump cell control unit)
57, 61 . . . heater drive circuit, CPU (heater control unit)
110 . . . Ip1 cell (oxygen pump cell)
130 . . . Ip2 cell (detection cell)
131 . . . solid electrolyte body
132, 133 . . . a pair of electrodes
161 . . . heater element (heater)

The entire contents of Japanese Patent Applications No. 2018-110023 filed on Jun. 8, 2018 is incorporated herein by reference.

Although the invention has been described above by reference to certain embodiment of the invention, the invention is not limited to the embodiment described above. Modifications and variations of the embodiment described above will occur to those skilled in the art in light of the above teachings. The scope of the invention is defined with reference to the following claims.

What is claimed is:

1. A NOx sensor control device connected to a NOx sensor mounted in an internal combustion engine, the NOx sensor having a detection cell configured to detect a NOx concentration and having a solid electrolyte body and a pair of electrodes provided on a surface of the solid electrolyte body and a heater heating the detection cell, the NOx sensor control device comprising:
a heater control unit configured to, at a time when an operation of the internal combustion engine stops, perform a recovery control of the NOx sensor which is an electric current control of the heater for removing SOx adsorbed to the NOx sensor.

2. The NOx sensor control device as claimed in claim 1, wherein:
the heater control unit is configured to, at the time when the operation of the internal combustion engine stops, control the heater so that a temperature of the heater becomes a second control temperature that is higher than a first control temperature of the heater during the operation of the internal combustion engine.

3. The NOx sensor control device as claimed in claim 1, wherein:
the heater control unit is configured to judge, on the basis of an operation signal of the internal combustion engine, that the operation of the internal combustion engine stops.

4. The NOx sensor control device as claimed in claim 1, wherein:
the heater control unit is configured to perform the recovery control at a predetermined timing with the operation of the internal combustion engine regarded as a stop.

5. The NOx sensor control device as claimed in claim 1, wherein:
the heater control unit is configured to stop the recovery control when receiving an operation signal of the internal combustion engine.

6. The NOx sensor control device as claimed in claim 2, wherein:
the second control temperature is set so that a temperature of the detection cell is 730° C. or higher.

7. The NOx sensor control device as claimed in claim 1, wherein:
the NOx sensor further has an oxygen pump cell configured to perform pump-out and/or pump-in of oxygen between an inside and an outside of the NOx sensor, and
the NOx sensor control device further comprises:
an oxygen pump cell control unit configured to operate the oxygen pump cell so as to pump out the oxygen from the NOx sensor when the heater control unit performs the recovery control.

8. The NOx sensor control device as claimed in claim 1, wherein:
the heater control unit is configured to stop the control of the heater when a totalizing control time of the recovery control is a predetermined threshold value or more.

9. The NOx sensor control device as claimed in claim 2, wherein:
the heater control unit is configured to set completion related information that indicates completion of the control when a totalizing control time of the recovery control is a predetermined threshold value or more, and
the heater control unit is configured to stop the recovery control on the basis of the completion related information when receiving no operation signal of the internal combustion engine after setting the completion related information.

10. The NOx sensor control device as claimed in claim 4, wherein:
the heater control unit is configured to set recovery process information that indicates that the recovery control is ongoing at present, and to continue totalizing a time until the timing comes, and
when the time is totalized until the timing comes, the heater control unit is configured to clear the totalized time when starting the recovery control, and to continue performing the recovery control on the basis of the recovery process information.

11. A method of controlling a NOx sensor mounted in an internal combustion engine, the NOx sensor having a detection cell configured to detect a NOx concentration and having a solid electrolyte body and a pair of electrodes provided on a surface of the solid electrolyte body and a heater heating the detection cell, the method comprising:
at a time when an operation of the internal combustion engine stops, performing an electric current control of the heater for removing SOx adsorbed to the NOx sensor.

* * * * *